US006939965B2

(12) United States Patent
Painter et al.

(10) Patent No.: US 6,939,965 B2
(45) Date of Patent: Sep. 6, 2005

(54) PROCESS OF MANUFACTURE OF 1,3-OXATHIOLANE NUCLEOSIDES USING TITANIUM TRICHLORIDE MONO-ISOPROPOXIDE (75) Inventors: George R. Painter, Chapel Hill, NC (US); Dennis C. Liotta, McDonough, GA (US); Merrick R. Almond, Apex, NC (US); Darryl G. Cleary, Chapel Hill, NC (US); José D. Soria, Decatur, GA (US); Marcos Sznaidman, Durham, NC (US)

(73) Assignees: Gilead Sciences, Inc., Foster City, CA (US); Emory University, Atlanta, GA (US)

( * ) Notice: Subject to any disclaimer, the term of this patent is extended or adjusted under 35 U.S.C. 154(b) by 0 days.

(21) Appl. No.: 10/361,980

(22) Filed: Feb. 11, 2003

(65) Prior Publication Data

US 2003/0144532 A1 Jul. 31, 2003

Related U.S. Application Data (60) Continuation of application No. 09/570,885, filed on May 15, 2000, now Pat. No. 6,518,425, which is a division of application No. 09/373,891, filed on Aug. 12, 1999, now Pat. No. 6,215,004.
(60) Provisional application No. 60/122,841, filed on Mar. 3, 1999, and provisional application No. 60/096,214, filed on Aug. 12, 1998.

(51) Int. Cl.[7] .................... C07D 473/16; C07D 473/18; C07D 473/34; C07D 473/40; C07D 487/04
(52) U.S. Cl. ........................ 544/276; 544/277; 544/312; 544/314; 544/317; 544/318
(58) Field of Search ................................ 544/226, 277, 544/312, 314, 317, 318

(56) References Cited

U.S. PATENT DOCUMENTS

| 5,041,449 | A | 8/1991 | Belleau |
| 5,047,407 | A | 9/1991 | Belleau |
| 5,204,466 | A | 4/1993 | Liotta et al. |
| 5,210,085 | A | 5/1993 | Liotta et al. |
| 5,234,913 | A | 8/1993 | Furman et al. |
| 5,248,776 | A | 9/1993 | Chu |
| 5,276,151 | A | 1/1994 | Liotta |
| 5,466,806 | A | 11/1995 | Belleau et al. |
| 5,486,520 | A | 1/1996 | Belleau et al. |
| 5,538,975 | A | 7/1996 | Dionne |
| 5,539,116 | A | 7/1996 | Liotta |
| 5,587,480 | A | 12/1996 | Belleau et al. |
| 5,618,820 | A | 4/1997 | Dionne |
| 5,663,320 | A | 9/1997 | Mansour |
| 5,684,164 | A | 11/1997 | Belleau |
| 5,693,787 | A | 12/1997 | Mansour |
| 5,696,254 | A | 12/1997 | Mansour |
| 5,700,937 | A | 12/1997 | Liotta et al. |
| 5,728,575 | A | 3/1998 | Liotta et al. |
| 5,744,596 | A | 4/1998 | Mansour |
| 5,756,706 | A | 5/1998 | Mansour |
| 5,763,606 | A | 6/1998 | Mansour |
| 5,814,639 | A | 9/1998 | Liotta et al. |
| 5,827,727 | A | 10/1998 | Liotta et al. |
| 5,892,025 | A | 4/1999 | Liotta et al. |
| 5,914,331 | A | 6/1999 | Liotta et al. |
| 5,914,400 | A | 6/1999 | Liotta et al. |
| 5,922,867 | A | 7/1999 | Mansour et al. |

FOREIGN PATENT DOCUMENTS

| EP | 0 515 144 | 11/1992 |
| EP | 0 526 253 | 2/1993 |
| EP | 0 337 713 | 10/1995 |
| EP | 0 382 526 | 5/1996 |
| EP | 0 711 771 | 5/1996 |
| EP | 0 515 156 | 7/1996 |
| EP | 0 513 200 B1 | 9/1998 |
| EP | 0 872 237 | 10/1998 |
| WO | WO 91/11186 | 8/1991 |
| WO | WO 91/17159 | 11/1991 |
| WO | WO 92/14743 | 9/1992 |
| WO | WO 92/15308 | 9/1992 |
| WO | WO 92/15309 | 9/1992 |
| WO | WO 92/18517 | 10/1992 |
| WO | WO 94/09793 | 5/1994 |
| WO | WO 96/30369 | 10/1996 |

OTHER PUBLICATIONS

Norbeck, et al., *Tetrahedron Letters*, 1989, p. 6246, 30(46).
Schinazi, et al., "Selective Inhibition of Human Immunodeficiency Viruses by Racemates and Enantiomers of cis–5–Fluoro–1–[2–(Hydroxymethyl)–1, 3–Oxathiolane–5–5–yl]Cytosine," *Antimicrobial Agents and Chemotherapy*, Nov. 1992, p. 2423–2431.
Kraus et al., "Synthesis of New 2,5–Disubstitued 1,3–Oxathiolanes Intermediates in Nucleoside Chemistry," *Synthesis*, 1991, p. 1046–1048.
McIntosh, et al., "2 Mercaptoaldehyde Dimers and 2,5–Dihydrothiophenes from 1,2–Oxathiolan–5–Ones," *Can. J. Chem.*, 1983, p. 1872–1875, vol. 61.
Belleau, et al., "Oxadative Degradation of L–Ascorbic Acid Acetals to 2',3'–Dideoxy–3'–Oxaribofuranoside. Synthesis of Enantiomerically Pure 2',3'–Dideoxy–3'Oxacytidine Stereoisomers as Potential Antiviral Agents," *Tetrahedron Letters*, 1992, p. 6949–6952, vol. 33, No. 46.
Choi, et al., "In Situ complexation Directs the Stereochemistry of N–Glycosylation in the Synthesis of Oxathiolanyl and Dioxolanyl Nucleoside Analogues," *J. Am. Chem. Soc.*, 1991, p. 9377–9379, 213.
Du, Jinfa et al., *Nucleosides and Nucleotides*, vol. 17, 1–3.
Jones, *Can. J. Chem.* vol. 61, 1872–1875 (1983).
Hoong, et al., *J. Org. Chem.*, 57:5563–5565 (1992).

Primary Examiner—Thomas C. McKenzie
(74) Attorney, Agent, or Firm—Sherry M. Knowles, Esq.; King & Spalding, LLP (57) ABSTRACT Processes for the preparation of 1,3-oxathiolane nucleosides are provided that include reacting a 5-O-protected-oxymethyl-1,3-oxathiolane with a silylated nucleoside in the presence of $(Cl)_3Ti(isopropoxide)$. Using the processes described herein, the compounds can be provided as isolated enantiomers.

14 Claims, 3 Drawing Sheets

PROCESS OF MANUFACTURE OF 1,3-OXATHIOLANE NUCLEOSIDES USING TITANIUM TRICHLORIDE MONO-ISOPROPOXIDE

This application is a continuation application of U.S. patent application Ser. No. 09/570,885 filed on May 15, 2000, issued on Feb. 11, 2003 as U.S. Pat. No. 6,518,425, which is a divisional application of U.S. Ser. No. 09/373,891 filed on Aug. 12, 1999, issued on Apr. 10, 2001 as U.S. Pat. No. 6,215,004.

This application is in the area of methods for the manufacture of 1,3-oxathiolane nucleosides and claims priority to U.S. provisional applications Ser. No. 60/096,214, filed on Aug. 12, 1998 and Ser. No. 60/122,841, filed on Mar. 3, 1999.

BACKGROUND OF THE INVENTION

The success of various synthetic nucleosides such as AZT, D4T, DDI, and DDC in inhibiting the replication of HIV in vivo or in vitro led researchers in the late 1980's to design and test nucleosides that substitute a heteroatom for the carbon atom at the 3'-position of the nucleoside. Norbeck, et al., disclosed that (±)-1-[cis-(2,4)-2-(hydroxymethyl)-4-dioxolanyl]thymine (referred to as (±)-dioxolane-T) exhibits a modest activity against HIV ($EC_{50}$ of 20 $\mu$M in ATH8 cells), and is not toxic to uninfected control cells at a concentration of 200 $\mu$M. *Tetrahedron Letters* 30 (46), 6246, (1989). European Patent Application Publication No. 337 713 and U.S. Pat. No. 5,041,449, assigned to BioChem Pharma, Inc., disclose racemic 2-substituted-4-substituted-1,3-dioxolanes that exhibit antiviral activity. Published PCT application numbers PCT US91/09124 and PCT US93/08044 disclose isolated β-D-1,3-dioxolanyl nucleosides for the treatment of HIV infection. WO 94/09793 discloses the use of isolated β-D-1,3-dioxolanyl nucleosides for the treatment of HBV infection.

Published PCT US95/11464 discloses that (−)-(2S,4S)-1-(2-hydroxymethyl-1,3-dioxolan-4-yl)cytosine is useful in the treatment of tumors and other abnormal cell proliferation.

U.S. Pat. No. 5,047,407 and European Patent Application Publication No. 0 382 526, also assigned to BioChem Pharma, Inc., disclose that a number of racemic 2-substituted-5-substituted-1,3-oxathiolane nucleosides have antiviral activity, and specifically report that the racemic mixture of 2-hydroxymethyl-5-(cytosin-1-yl)-1,3-oxathiolane (referred to below as BCH-189) has approximately the sane activity against HIV as AZT, with less toxicity. The (−)-enantiomer of BCH-189 (U.S. Pat. No. 5,539,116 to Liotta, et al.), known as 3TC, is now sold commercially for the treatment of HIV in humans in the United States. See also EP 513 200 B1.

It has also been disclosed that cis-2-hydroxymethyl-5-(5-fluorocytosin-1-yl)-1,3-oxathiolane ("FTC") has potent HIV activity. See Schinazi, et al., "Selective Inhibition of Human immunodeficiency viruses by Racemates and Enantiomers of cis-5-Fluoro-1-[2-(Hydroxymethyl)-1,3-Oxathiolane-5-yl]Cytosine" *Antimicrobial Agents and Chemotherapy*, November 1992, page 2423–2431. See also U.S. Pat. Nos. 5,814,639; 5,914,331; 5,210,085; U.S. Pat. No. 5,204,466, WO 91/11186, and WO 92/14743.

Because of the commercial importance of 1,3-oxathiolane nucleosides, a number of processes for their production have been described in patents and scientific literature. Three key aspects of the synthesis must be considered during design of the process. First, the reaction scheme must provide an efficient route to the 1,3-oxathiolane ring structure, preferably, with substituent groups in place for use in subsequent reactions. Second, the reaction scheme must provide an efficient means to condense the 1,3-oxathiolane ring with a suitably protected base, which, in the case of 3TC is cytosine, and in the case of FTC is 5-fluorocytosine. Third, the reaction must be stereoselective, i.e., it must provide the enantiomer of choice. The substituents on the chiral carbons (the specified purine or pyrimidine base (referred to as the C5 substituent) and $CH_2OH$ (referred to as the C2 substituent)) of the 1,3-oxathiolane nucleosides can be either cis (on the same side) or trans (on opposite sides) with respect to the oxathiolane ring system. Both the cis and trans racemates consist of a pair of optical isomers. Hence, each compound has four individual optical isomers. The four optical isomers are represented by the following configurations (when orienting the oxathiolane moiety in a horizontal plane such that the —S—$CH_2$— moiety is in back): (1) cis (also referred to as β), with both groups "up", which is the naturally occurring L-cis configuration (2) cis, with both groups "down", which is the non-naturally occurring β-cis configuration; (3) trans (also referred to as the α-configuration) with the C2 substituent "up" and the C5 substituent "down"; and (4) trans with the C2 substituent "down" and the C5 substituent "up". The two cis enantiomers together are referred to as a racemic mixture of β-enantiomers, and the two trans enantiomers are referred to as a racemic mixture of α-enantiomers. In general, it is fairly standard to be able to separate the pair of cis racemic optical isomers from the pair of trans racemic optical isomers. It is a significantly more difficult challenge to separate or otherwise obtain the individual enantiomers of the cis-configuration. For 3TC and FTC, the desired stereochemical configuration is the β-L-isomer.

Routes to Produce the 1,3-Oxathiolane Ring

The numbering scheme for the 1,3-oxathiolane ring is given below.

Kraus, et al., ("Synthesis of New 2,5-Disubstituted 1,3-Oxathiolanes. Intermediates in Nucleoside Chemistry", Synthesis, pages 1046–1048 (1991)) describe the problems associated with the reaction of an aldehyde of a glyoxylate or glycolic acid with mercaptoacetic acid in toluene in the presence of p-toluenesulfonic acid. Kraus notes that a requirement for the success of this reaction is that glycolic derivatives which exist in the hydrate form have to be converted into the free aldehyde by azeotropic removal of water with toluene before the cyclocondensation. Thereafter, to complete the reduction of both the lactone and carboxylic acid functions, different catalytic reductive reagents had to be employed. Reduction with sodium borohydride failed, and borane-methyl sulfide complex (BMS) was able to reduce only the carboxylic acid function. When the temperature was raised, or a large excess of BMS was used, ring opening occurred leading to polymeric material. Reduction of the 2-carboxy-1,3-oxathiolan-5-one with sodium bis(2-methoxyethoxy)aluminum hydride in toluene gave a mixture of products. Tributyl tin hydride gave no reduction. Finally, when the reduction was performed on the protected lactones, it was not possible to isolate the desired compound, regardless of the catalytic reductive conditions.

Because of these difficulties, Kraus, et al. proposed a reaction that involved the cyclocondensation of anhydrous glyoxylates with 2-mercaptoacetaldehyde diethyl acetal at reflux in toluene to produce 5-ethoxy-1,3-oxathiolane derivatives which could be reduced with BMS to give the corresponding 2-hydroxymethyl-1,3-oxathiolane in 50% yield, which after benzoylation provided a mixture of cis and trans 2-benzoyloxymethyl-5-ethoxy-1,3-oxathiolane. This process is also described in U.S. Pat. No. 5,047,407.

U.S. Pat. No. 5,248,776 discloses a method for the production of enantiomerically pure β-L-1,3-oxathiolane nucleosides from 1,6-thioanyhydro-L-gulose.

U.S. Pat. No. 5,204,466 discloses a route to prepare the 1,3-oxathiolane ring via the reaction of mercaptoacetic acid (thioglycolic acid) with a glycoaldehyde to form 2-(R-oxy)-methyl-5-oxo-1,3-oxathiolane.

U.S. Pat. No. 5,466,806 describes a process for preparing a 2-hydroxymethyl-5-hydroxy-1,3-oxathiolane via the reaction of the dimer of mercaptoacetaldehyde with a compound of the formula $R_wOCH_2CHO$ under neutral or basic conditions, wherein $R_w$ is a hydroxyl protecting group. See also McIntosh, et al, "2-Mercaptoaldehyde dimers and 2,5-dihydrothiophenes from 1,2-oxathiolan-5-ones," *Can. J. Chem.* Vol 61, 1872–1875 (1983).

Belleau, et al., disclosed a method to prepare a 1,3-dioxolane nucleoside via the oxidative degradation of L-ascorbic acid. Belleau, et al., "Oxidative Degradation of L-ascorbic Acid Acetals to 2',3'-Dideoxy-3'-Oxaribofuranosides. Synthesis of Enantiomerically Pure 2',3'-Dideoxy-3'-Oxacytidine Stereoisomers as Potential Antiviral Agents.," *Tetrahedron Letters*, vol 33, No. 46, 6949–6952 (1992).

U.S. Pat. No. 5,204,466 discloses the preparation of a 1,3-oxathiolane ring via ozonolysis of an allyl ether or ester having the formula $CH_2=CHCH_2OR$, in which R is a protecting group, to form a glycoaldehyde having the formula $OHCCH_2OR$, and adding thioglycolic acid to the glycoaldehyde to form a lactone of the formula 2-R-oxy)-methyl-5-oxo-1,3-oxathiolane.

Routes to Condense the 1,3-oxathiolane with the Protected Base

U.S. Pat. No. 5,204,466 discloses a method to condense a 1,3-oxathiolane with a protected pyrimidine base using tin chloride as a Lewis acid, which provides virtually complete β-stereoselectivity. See also Choi, et al, "In Situ Complexation Directs the Stereochemistry of N-Glycosylation in the synthesis of Oxathiolanyl and Dioxolanyl Nucleoside Analogues," *J. Am. Chem. Soc.* 1991, 213, 9377–9379. The use of tin chloride creates undesirable residues and side products during the reaction which are difficult to remove.

A number of U.S. patents disclose a process for the preparation of 1,3-oxathiolane nucleosides via the condensation of a 1,3-oxathiolane intermediate that has a chiral ester at the 2-position of the ring, with a protected base in the presence of a silicon-based Lewis acid. The ester at the 2-position must then be reduced to the corresponding hydroxymethyl group to afford the final product. See U.S. Pat. Nos. 5,663,320; 5,864,164; 5,693,787; 5,696,254; 5,744,596; and 5,756,706.

U.S. Pat. No. 5,763,606 discloses a process for producing predominantly cis-2-carboxylic or thiocarboxylic acid 1,3-oxathiolane nucleosides that includes coupling a desired, previously silylated purine or pyrimidine base with a bicyclic intermediate in the presence of a Lewis acid.

U.S. Pat. No. 5,272,151 describes a process for the preparation of 1,3-dioxolane nucleosides that includes reacting a 2-O-protected-5-O-acylated-1,3-dioxolane with an oxygen- or nitrogen-protected purine or pyrimidine base in the presence of a titanium catalyst.

Choi, et al, "In Situ Complexation Directs the Stereochemistry of N-Glycosylation in the synthesis of Oxathiolanyl and Dioxolanyl Nucleoside Analogues," *J. Am Chem. Soc.* 1991, 213, 9377–9379, reported that no coupling of the 1,3-oxathiolane with protected pyrimidine base occurs with $HgCl_2$, $Et_2AlCl$, or $TiCl_2(O\text{-isopropyl})_2$ (see footnote 2). Choi also reported that the reaction between anomeric 1,3-oxathiolane acetates with silylated cytosine and virtually any common Lewis acid other than tin chloride resulted in the formation of inseparable mixtures of N-glycosylated anomers.

U.S. Pat. No. 5,922,867 discloses a method for preparing a dioxolane nucleoside that includes glycosylating a purine or pyrimidine base with a 2-protected-oxymethyl-4-halo-1,3-dioxolane.

Routes to Provide the 1,3-Oxathiolane Nucleoside in the Desired Stereoconfiguration U.S. Pat. No. 5,728,575 claims the method to obtain 3TC and FTC via enzymatic resolution of the 5'-acyl protected racemic nucleoside using pig liver esterase, porcine pancreatic lipase, or subtilisin. U.S. Pat. No. 5,539,116 claims 3TC, the product of the resolution process of the '575 patent.

U.S. Pat. No. 5,827,727 to Liotta claims the method to obtain 3TC and FTC via stereoselective deamination using cytidine deaninase.

U.S. Pat. No. 5,892,025 to Liotta, et al. claims a method for the resolution of the combination of the enantiomers of cis-FTC by passing the cis-FTC through an acetylated β-cyclodextrin chiral column.

U.S. Pat. No. 5,663,320 claims a process for producing a chiral 1,3-oxathiolane intermediate that includes resolving the racemic intermediate with a chiral auxiliary.

In light of the importance of 1,3-oxathiolane nucleosides in the treatment of human immunodeficiency virus and hepatitis B virus, it is an object of the present invention to provide a process for the production of 1,3-oxathiolane nucleosides which can be used on a manufacturing scale.

SUMMARY OF THE INVENTION

Processes for the preparation of 1,3-oxathiolane nucleosides are provided that include efficient methods for the preparation of the 1,3-oxathiolane ring and subsequent condensation of the 1,3-oxathiolane with a pyrimidine or purine base. Using the processes described herein, the compound can be provided as an isolated enantiomer.

It has been discovered that $2\text{-}[R^1C(O)OCH_2]\text{-}1,3\text{-}$oxathiolanyl-5-one can be prepared in high yield by directly reacting an acetal of the formula $(alkylO)_2CHR$, wherein R is $-(CH_2-O-C(O)R^2)$, and $R^1$ and $R^2$ are independently alkyl, aryl, heteroaryl, alkaryl, alkylheteroaryl or aralkyl, with mercaptoacetic acid in the presence of a Lewis or protic acid in an organic solvent with a minimum amount of water. The acetal can be used as a mixture of the hemiacetal, the acetal monomer or higher condensation products thereof. By reacting the mercaptoacetic acid directly with the acetal, side products are decreased, which increases product purity and yield of this starting material.

$(R^1O)_2CHR$ can be prepared by any appropriate route, and for example by either (i) reaction of a compound of the formula $OH-CH_2-C=C-CH_2-OH$ with $RC(O)Cl$ to form $RC(O)OCH_2C(H)=C(H)OC(O)R$, which is ozonized or otherwise cleaved to form the desired compound: or (ii) reduction of $(R^1O)_2CHC(O)H$ to form $(R^1O)_2CHCH_2OH$, which is reacted with $ClC(O)R$ to form the desired compound.

In another alternative route, HC(O)CH$_2$OC(O)R$^1$ is reacted with mercaptoacetic acid to form the desired 1,3-oxathiolane ring. HC(O)CH$_2$OC(O)R$^1$ can be prepared by any appropriate route, and for example, by the methods A and B illustrated in FIG. 2.

The 5-(O protecting group)-2-protected hydroxymethyl-1,3-oxathiolane or its 5-acetyloxy derivative can be condensed with a protected silylated pyrimidine or purine base, including cytosine or 5-fluorocytosine, using a Lewis acid such as tin chloride, (Cl)$_3$Ti(isopropoxide), trimethylsilyl triflate, trimethylsilyl iodide, or other Lewis acid known to catalyze the condensation, including those Lewis acids described in U.S. Pat. Nos. 5,663,320; 5,864,164; 5,693,787; 5,696,254; 5,744,596; and 5,756,706 to provide the corresponding nucleoside with high β-selectivity. It is surprising that (Cl)$_3$Ti(isopropoxide) is useful as a catalyst for condensation of the 1,3-oxathiolane with the protected base, given that it has been reported that no coupling of the 1,3-oxathiolane with protected pyrimidine base occurs with HgCl$_2$, Et$_2$AlCl, or TiCl$_2$(O-isopropyl)$_2$.

In an alternative embodiment, glycolic acid is substituted for mercaptoacetic acid in the presence of a Lewis acid to form the corresponding 1,3-dioxolane, which can be condensed with a purine or pyrimidine base to provide a 1,3-dioxolane nucleoside. It is preferred to conduct the cyclocondensation of an acetal (or aldehyde) with glycolic acid in the presence of a Lewis acid such as boron trifluoride diethyl etherate rather than a protic acid such as p-toluenesulfonic acid.

It has also been discovered that a 1,3-oxathiolane nucleoside can be produced by: (i) preparing a 5-halo-2-protected-oxymethyl-1,3-oxathiolane; and (ii) reacting the 5-halo-2-protected-oxymethyl-1,3-oxathiolane with a protected purine or pyrimidine base at low temperature, and preferably below 25 degrees Celsius, and more preferably below 10 degrees Celsius. It was surprising that the condensation reaction can be carried out effectively without the aid of a Lewis acid. In a preferred embodiment, the halogen in the 5-position of the oxathiolane is a chloro substituent. The reaction typically produces a mixture of β and α anomers that must be separated. The β anomer typically is produced in excess over the α anomer. The separation of β and α anomers can be effected by any known method, including fractional crystallization, chromatography (achiral or chiral), or the preparation and separation of diastereomeric derivatives. In one embodiment, a racemic 5-acylated-2-protected-oxymethyl-1,3-oxathiolane is chlorinated at low temperature (e.g., 0 degrees Celsius), and then condensed with a protected base such as 5-fluorocytosine or cytosine, to produce a mixture of diastereomers (with the β compound typically in substantial excess). In another embodiment, a chiral 5-acylated-2-protected-oxymethyl-1,3-oxathiolane is chlorinated and then reacted with a protected base. Any 5-acylated-2-protected-oxymethyl-1,3-oxathiolane can be used that provides the desired product. Nonlimiting examples of appropriate acyl moieties include, but are not limited to acetate, propionate, butyrate, benzoate, p-methoxybenzoate, and p-(t-butyl)-benzoate. The halogenaton reaction can be carried out in any useful organic solvent, including toluene, chloroform, acetic acid, tetrahydrofuran, ether, benzene, etc. The anomeric ratio of α to β produced in the condensation reaction can be affected by the solvent selected for use in the reaction. One can easily test various organic solvents to select that solvent which provides the optimal yield of the desired product.

DETAILED DESCRIPTION OF THE INVENTION

A process for the preparation of 1,3-oxathiolane nucleosides is provided that includes efficient methods for the preparation of the 1,3-oxathiolane ring and subsequent condensation of the 1,3-oxathiolane with a pyrimidine or purine base.

It has been discovered that 2-[R$^1$C(O)OCH$_2$]-1,3-oxathiolanyl-5-one can be prepared in high yield by directly reacting an acetal of the formula (alkylO)$_2$CHR, wherein R is —(CH$_2$—O—C(O)R$^2$), and is R$^1$ and R$^2$ are independently alkyl, aryl, heteroaryl, alkaryl, alkylheteroaryl or aralkyl, with mercaptoacetic acid in the presence of a Lewis or protic acid in an organic solvent with a minimum amount of water. The acetal can be used as a mixture of the hemiacetal, the acetal monomer or higher condensation products thereof. By reacting the mercaptoacetic acid directly with the acetal, side products are decreased, which increases product purity and yield of this starting material.

The 5-(O protecting group)-2-protected hydroxymethyl-1,3-oxathiolane or its 5-acetyloxy derivative can be condensed with a protected silylated pyrimidine or purine base, including cytosine or 5-fluorocytosine, using a Lewis acid such as tin chloride, (Cl)$_3$Ti(isopropoxide), trimethylsilyl triflate, trimethylsilyl iodide, or other Lewis acid known to catalyze the condensation, including those Lewis acids described in U.S. Pat. Nos. 5,663,320; 5,864,164; 5,693,787; 5,696,254; 5,744,596; and 5,756,706 to provide the corresponding nucleoside with high β-selectivity. It is surprising that (Cl)$_3$Ti(isopropoxide) is useful as a catalyst for condensation of the 1,3-oxathiolane with the protected base, given that it has been reported that no coupling of the 1,3-oxathiolane with protected pyrimidine base occurs with HgCl$_2$, Et$_2$AlCl, or TiCl$_2$(O-isopropyl)$_2$.

In an alternative embodiment, glycolic acid is substituted for mercaptoacetic acid to form the corresponding 1,3-dioxolane, which can be condensed with a purine or pyrimidine base to provide a 1,3-dioxolane nucleoside. It is preferred to conduct the cyclocondensation of an acetal (or aldehyde) with glycolic acid in the presence of a Lewis acid such as boron trifluoride diethyl etherate rather than a protic acid such as p-toluenesulfonic acid.

It has also been discovered that a 1,3-oxathiolane nucleoside can be produced by (i) preparing a 5-acylated-2-protected-oxymethyl-1,3-oxathiolane and (ii) reacting the 5-halo-2-protected-oxymethyl-1,3-oxathiolane with a protected purine or pyrimidine base at low temperature, and preferably below 25 degrees Celsius, and more preferably below 10 degrees Celsius. It was surprising that the condensation reaction can be carried out effectively without the aid of a Lewis acid. In a preferred embodiment, the halogen in the 5-position of the oxathiolane is a chloro substituent. The reaction typically produces a mixture of β and α anomers that must be separated. The β anomer typically is produced in excess over the α anomer. The separation of β and α anomers can be effected by any known method, including fractional crystallization, chromatography (achiral or chiral), or the preparation and separation of diastereomeric derivatives. In one embodiment, a racemic 5-acylated-2-protected-oxymethyl-1,3-oxathiolane is chlorinated at low temperature (e.g., 0 degrees Celsius), and then condensed with a protected base such as 5-fluorocytosine or cytosine, to produce a mixture of diastereomers (with the β compound typically in substantial excess). In another embodiment, a chiral 5-acylated-2-protected-oxymethyl-1,3-oxathiolane is chlorinated and then reacted with a protected base. Any 5-acylated-2-protected-oxymethyl-1,3-oxathiolane can be used that provides the desired product. Nonlimiting examples of appropriate acyl moieties include, but are not limited to acetate, propionate, butyrate, benzoate, p-methoxybenzoate, and p-(t-butyl)-benzoate. The halogenation reaction can be carried out in any useful organic solvent, including toluene, chloroform, acetic acid, tetralydrofuran, ether, benzene, etc. The anomeric ratio of α to β produced in the condensation reaction can be affected by the solvent selected for use in the reaction. One can easily test various organic solvents to select that solvent which provides the optimal yield of the desired product.

The selected 5-acylated-2-protected-oxymethyl-1,3-oxathiolane can be halogenated to a 5-chloro, 5-bromo or 5-iodo derivative using known methods.

Chiral stationary phases for chiral chromatography are described in a number of texts, including for example, Stradi, et al., Analytical Enantioseparations, Polysaccaharides and their derivatives as chiral stationary phases. Perkin Elmer, 1992.

In place of the 5-acyl group, any other leaving group that can be displaced and substituted by halogen, and preferably chloride, can be used. Examples are alkoxy, alkoyxcarbonyl, amido, azido, and isocyanato.

I. Definitions

As used herein, the term "isolated enantiomer" refers to a nucleoside composition that includes at least approximately 95% to 100%, or more preferably, over 97% of a single enantiomer of that nucleoside.

The term purine or pyrimidine base, includes, but is not limited to, 6-alkylpurine and $N^6$-alkylpurines, $N^6$-acylpurines, $N^6$-benzylpurine, 6-halopurine, $N^6$-acetylenic purine, $N^6$-acyl purine, $N^6$-hydroxyalkyl purine, 6-thioalkyl purine, $N^2$-alkylpurines, $N^4$-alkylpyrimidines, $N^4$-acylpyrimidines, 4-halopyrimidines, $N^4$-acetylenic pyrimidines, 4-amino and $N^4$-acyl pyrimidines, 4-hydroxyalkyl pyrimidines, 4-thioalkyl pyrimidines, thymine, cytosine, 6-azapyrimidine, including 6-azacytosine, 2- and/or 4-mercaptopyrimidine, uracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, and pyrazolopyrimidinyl. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, acyl groups such as acetyl and propionyl, methanesulfonyl, and p-toluenesulfonyl. Preferred bases include cytosine, 5-fluorocytosine, uracil, thymine, adenine, guanine, xanthine, 2,6-diaminopurine, 6-aminopurine, 6-chloropurine and 2,6-dichloropurine.

The term alkyl, as used herein, unless otherwise specified, refers to a saturated straight, branched, or cyclic, primary, secondary, or tertiary hydrocarbon, typically of $C_1$ to $C_{18}$, and specifically includes methyl, ethyl, propyl, isopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of hydroxyl, carboxylic acid or ester, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991, hereby incorporated by reference.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis. Suitable protecting groups are described, for example, in Greene, et al., "Protective Groups in Organic Synthesis," John Wiley and Sons, Second Edition, 1991, hereby incorporated by reference.

The term aryl, as used herein, and unless otherwise specified, refers to phenyl, biphenyl, or naphthyl, and preferably phenyl. The aryl group can be optionally substituted with one or more moieties selected from the group consisting of hydroxyl, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., "Protective Groups in Organic Synthesis," John Wiley and Sons, Second Edition, 1991.

The term alkaryl or alkylaryl refers to an alkyl group with an aryl substituent.

The term aralkyl or arylalkyl refers to an aryl group with an alkyl substituent.

The term halo, as used herein, includes chloro, bromo, iodo, and fluoro.

The term acyl refers to moiety of the formula —C(O)R', wherein R' is alkyl; aryl, alkaryl, aralkyl, heteroaromatic, heterocyclic, alkoxyalkyl including methoxymethyl; arylalkyl including benzyl; aryloxyalkyl such as phenoxymethyl; aryl including phenyl optionally substituted with halogen, $C_1$ to $C_4$ alkyl or $C_1$ to $C_4$ alkoxy, or the residue of an amino acid.

As used herein, a leaving group means a functional group that is cleaved from the molecule to which it is attached under appropriate conditions.

The term heteroaryl or heterocyclic, as used herein, refers to a cyclic moiety that includes at least one sulfur, oxygen, or nitrogen in the ring. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isoxazolyl, pyrrolyl, quinazolinyl, pyridazinyl, pyrazinyl, cinnolinyl, phthalazinyl, quinoxalinyl, xanthinyl, hypoxanthinyl, and pteridinyl. Functional oxygen and nitrogen groups on the heterocyclic base can be protected as necessary or desired. Suitable protecting groups are well known to those skilled in the art, and include trimethylsilyl, dimethylhexylsilyl, The alkyl group can be optionally substituted with one or more moieties selected from the group consisting of hydroxyl, carboxylic acid or ester, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al, "Protective Groups in Organic Synthesis," John Wiley and Sons, Second Edition, 1991, hereby incorporated by reference.

The term alkylheteroaryl refers to an alkyl group substituted by a heteroaryl substituent.

II. Preparation of 1,3-Oxathiolane Lactone Ring

Figure 1:
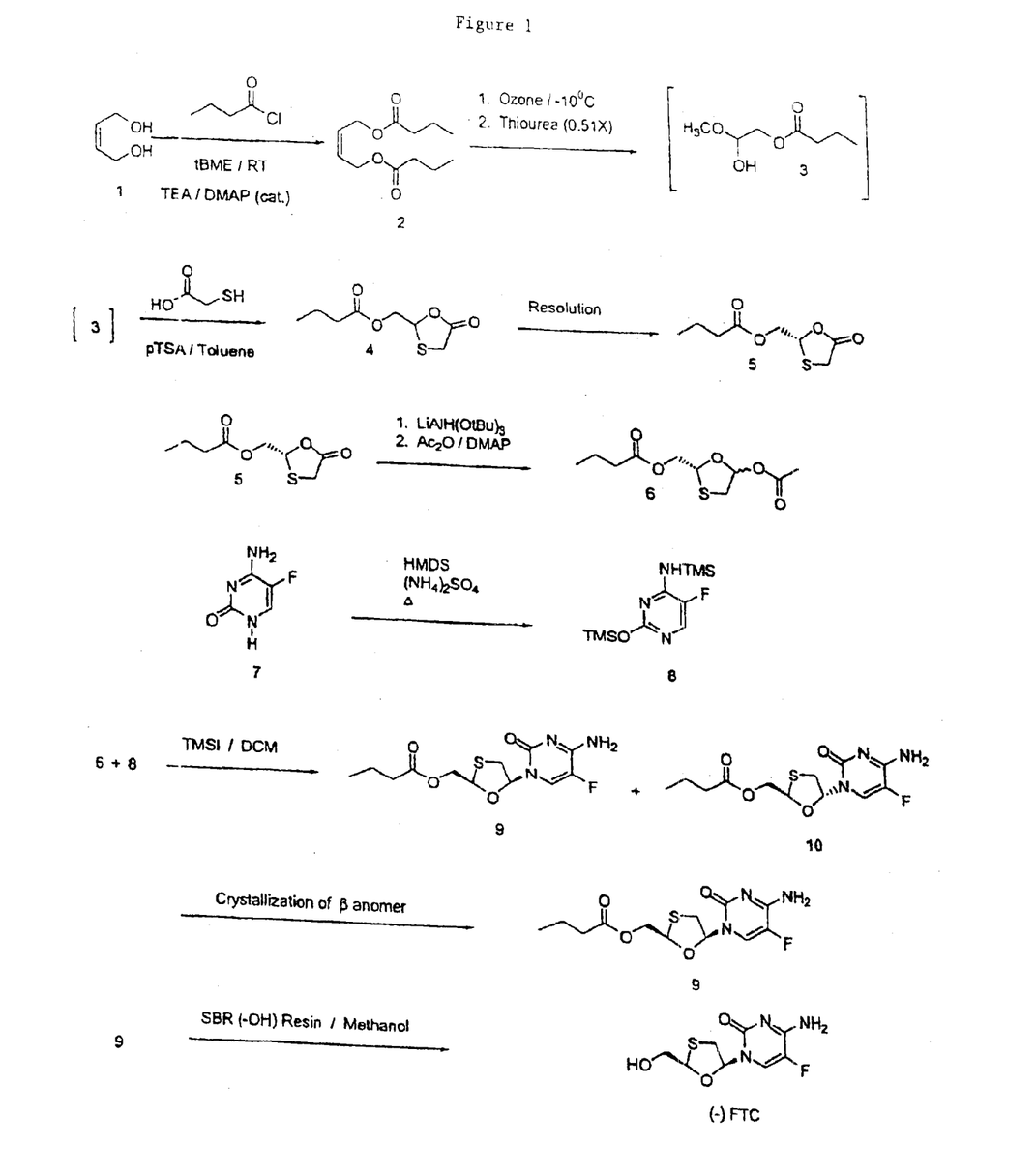
FIG. 1 is an illustration of one method for the preparation of a 1,3-oxathiolane nucleoside according to the present invention, that includes preparing 2-[R$^1$C(O)OCH$_2$]-1,3-oxathiolanyl-5-one by reacting a hemiacetal of the formula (R$^1$O)(OH)CHR wherein R is —(CH$_2$—O—C(O)R$^2$), with mercaptoacetic acid.

FIG. 1 illustrates one route for carrying out the disclosed process. 2-Butene-1,4-diol is reacted with a carboxylic acid chloride or other ester precursor to provide a 2-butene-1,4-diol diester. The selection of the carboxylic acid chloride or other ester precursor will be governed by the group desired at the 2-position of the resulting 1,3-oxathiolane ring. For example, if butyryl chloride is reacted with 2-butene-1,4-diol, in the resulting 2-[$R^1$C(O)OCH$_2$O]-1,3-oxathiolanyl-5-one, $R^1$ will be propyl. In other embodiments, the carboxylic acid chloride or other ester precursor is selected such that $R^1$ is alkyl, aryl, heteroaryl, alkaryl, alkheteroaryl or aralkyl.

In the second step of the reaction, the 2-butene-1,4-diester is cleaved, preferably by ozonolysis, to provide an acetal of the formula (alkylO)$_2$CHR or hemiacetal of the formula (alkylO)(OH)CHR, wherein R is —(CH$_2$—O—C(O)$R^2$), and $R^1$ and $R^2$ are independently alkyl, aryl, heteroaryl, alkaryl, alkylheteroaryl or aralkyl. Ozonolysis reactions are typically carried out at very low temperatures, usually, −70° C. or less. By carrying out the reaction at a higher temperature, perhaps −10° C., specialized low temperature reactors are not needed. The reaction affording the acetal or hemiacetal can be run in a variety of alcoholic solvents with or without co-solvents such as dichloromethane. The preferred alcoholic solvent is methanol. Ozonolysis reactions are often quenched with dimethyl sulfide, however, the use of thiourea has been found to afford the desired product in higher purity.

Alternatively, an acetal of the formula (alkylO)$_2$CHR, wherein R is (CH$_2$OC(O)$R^2$) and $R^1$ and $R^2$ are independently alkyl, aryl, heteroaryl, alkylheteroaryl, or aralkyl, can be prepared by acylation of (alkylO)$_2$CHCH$_2$OH with an appropriate acid halide or anhydride in the presence of a base such as triethylamine.

In a key step of the process, the acetal is then directly reacted with mercaptoacetic acid in the presence of a Lewis or protic acid in an organic solvent with a minimum amount of water. The acetal can be used as a mixture of the hemiacetal, the acetal monomer or higher condensation products thereof. Any protic acid or Lewis acid that provides the desired results is appropriate for use in this process. It has been found that the cyclocondensation of an acetal with mercaptoacetic acid efficiently provides a 1,3-oxathiolane. Conversely, the cyclocondensation of an aldehyde with mercaptoacetic acid is often times problematic affording much lower yields of desired 1,3-oxathiolane contaminated with unreacted aldehyde as well as aldehyde by-products.

In the next step, the 2-protected hydroxymethyl-5-oxo-1,3-oxathiolane is resolved by a number of available methods which are known in the art. The 2-substituent can be selected on the basis of ease of resolution at this stage. The group, for example, can be one known to be cleaved stereoselectively by an enzyme. U.S. Pat. No. 5,204,466 to Liotta, et al., describes a method to resolve the oxathiolane by enzymatic stereoselective hydrolysis using porcine pancreatic lipase, subtilisin, or pig liver esterase. U.S. Pat. No. 5,663,320 claims a process for producing a chiral 1,3-oxathiolane intermediate that includes resolving the racemic intermediate with a chiral auxiliary. WO 91/17159 discloses the use of cellulose triacetate or β-cyclodextrin chiral columns to separate the enantiomers of the 1,3-oxathiolane nucleosides.

The desired isolated (2R)-enantiomer of the 2-protected hydroxymethyl-5-oxo-1,3-oxathiolane, which in the case of 3TC and FTC, provides the β-L-enantiomer is reduced to the corresponding 5-O-protected compound, for example, the 5-acetate, using a reducing agent, preferably lithium tri-tert-butoxyaluminum hydride.

Figure 2:
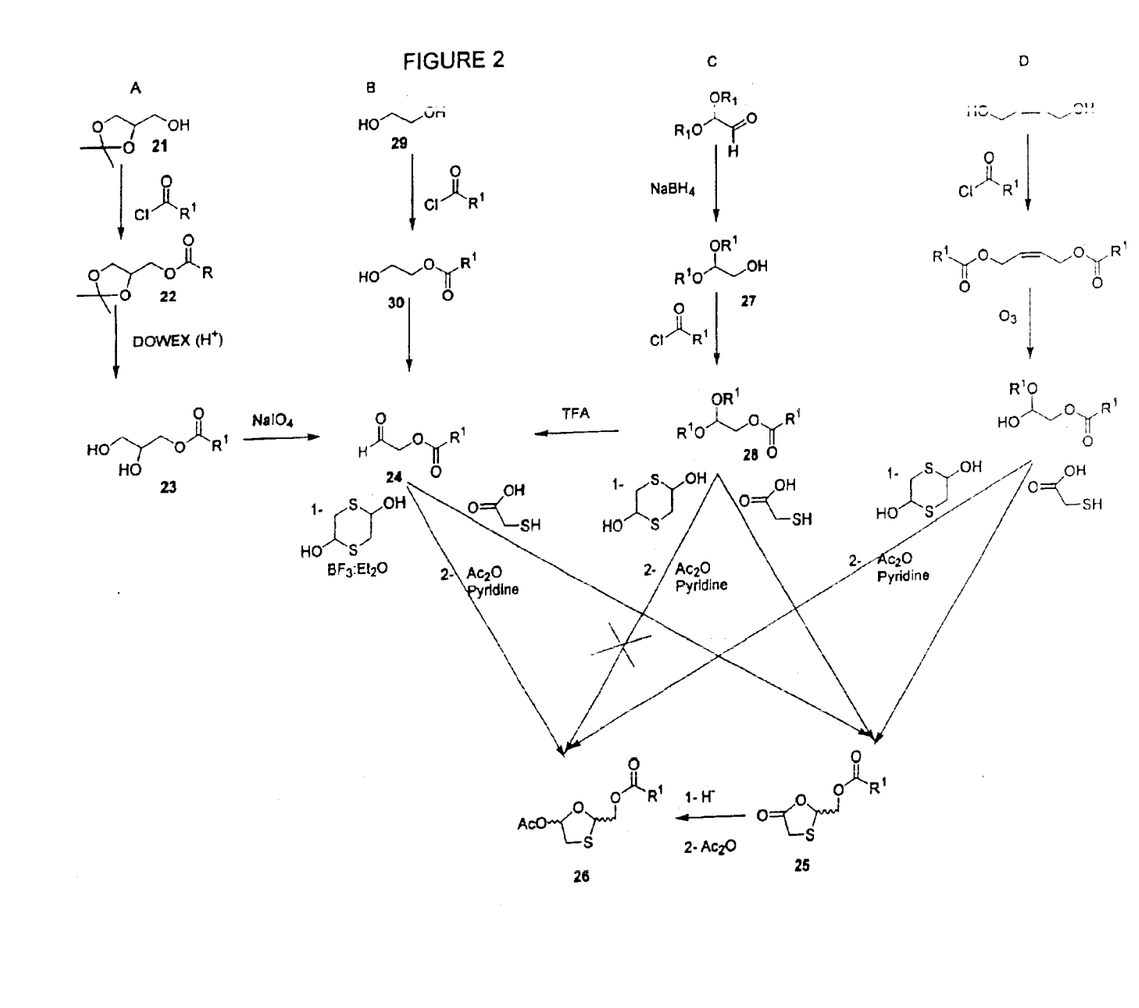
FIG. 2 is a schematic illustration of four alternative methods (A–D) for the preparation of a 1,3-oxathiolane ring according to the present invention.
Figure 3:
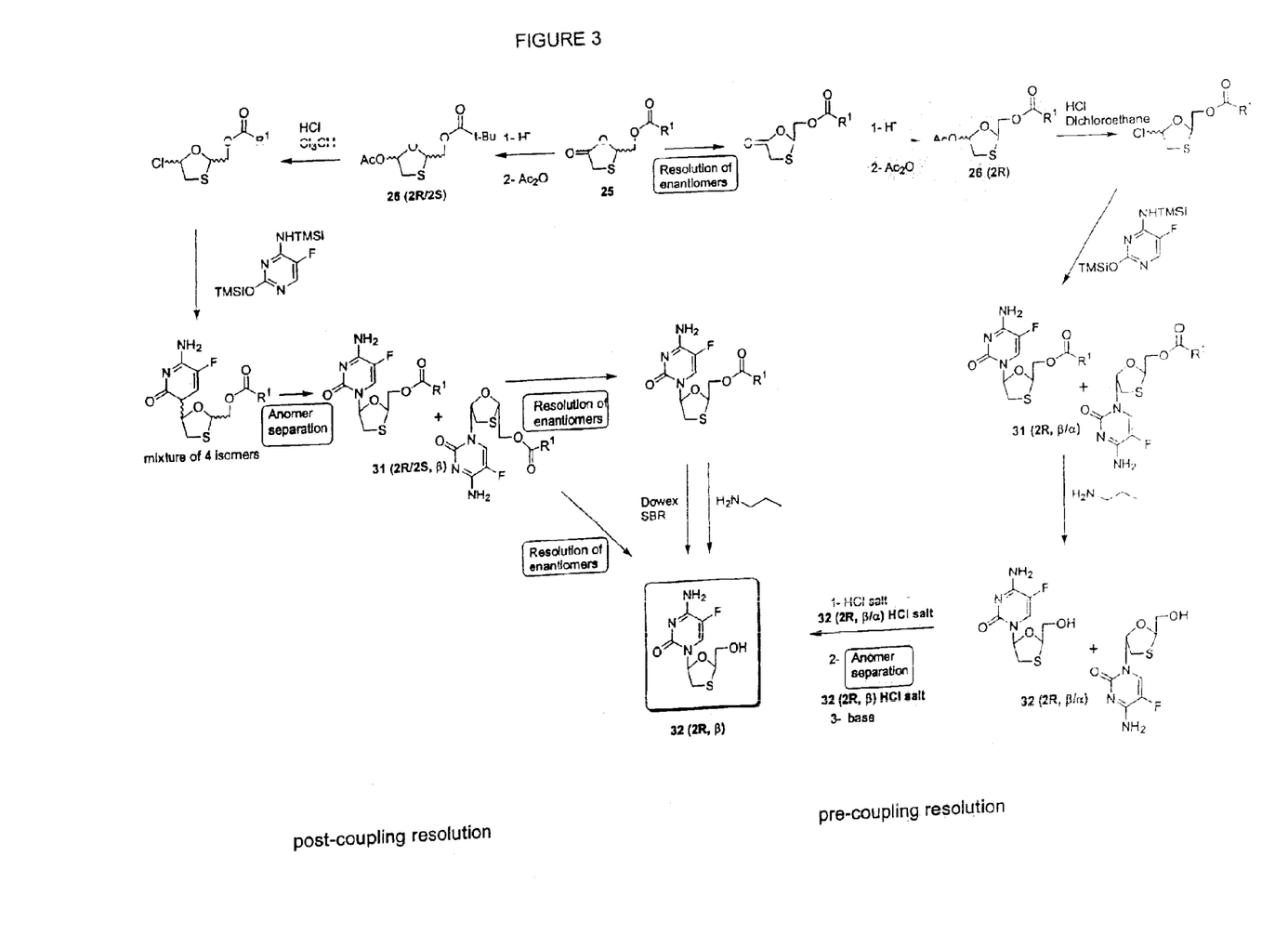
FIG. 3 is a schematic illustration of the preparation of 1,3-oxathiolane nucleoside enantiomers using pre- and post-coupling resolution.

FIG. 2 illustrates four additional embodiments (methods A–D) for preparing the 1,3-oxathiolane ring. As a nonlimiting illustrative example of method A in FIG. 2, (5-oxo-1,3-oxathiolan-2-yl) methyl butanoate can be prepared by a four-step process which does not require purification of the intermediate products. In a first step, (2,2-dimethyl-1,3-dioxolan-4-yl) methyl butanoate is prepared from solketal and n-butyryl chloride in t-butyl methyl ether, DMAP and triethylamine. The (2,2-dimethyl-1,3-dioxolan-4-yl) methyl butanoate is then placed in solution with Dowex 50W X8-100 H$^+$ resin in methanol, to yield 2,3-dihydroxypropyl butanoate. The resulting diol is then reacted with a solution of sodium periodate in distilled water to produce 2-oxoethyl butanoate. Using 2-oxoethyl butanoate, the (5-oxo-1,3-oxathiolan-2-yl) methyl butanoate can be prepared by reaction with mercaptoacetic acid as p-TsOH.H$_2$O in acetonitrile. The (5-oxo-1,3-oxathiolan-2-yl) methyl butanoate can be converted into its 5-acetyloxy derivative by reacting with lithium tri-t-butoxy aluminum hydride in THF.

As a nonlimiting example using method B in FIG. 2 to obtain the (5-oxo-1,3-oxathiolan-2-yl) methyl butanoate or its 5-acetyloxy derivative is to react 1,2-dihydroxy ethane with n-butyryl chloride in triethylamine. This reaction produces 2-hydroxyethyl butanoate, which is further reacted P$_2$O$_5$ in dry DCM, followed by DMSO and triethylamine to produce 2-oxyethyl butanoate. The 2-oxyethyl butanoate can be converted to the 5-acetyloxy derivative of (5-oxo-1,3-oxathiolan-2-yl) methyl butanoate by the process described above, or it can be converted into (5-oxo-1,3-oxathiolan-2-yl) methyl butanoate by reacting with mercaptoacetic acid and CSA in dry DCM.

As a nonlimiting example using method C in FIG. 2, (5-oxo-1,3-oxathiolan-2-yl) methyl butanoate or the 5-acetyloxy derivative thereof may be obtained from process which includes reacting 2,2-diethoxyethyl butanoate in DCM and treating with TFA and water. This reaction yields 2-oxoethylbutanoate, which may be reacted with mercaptoacetic acid in CSA and DCM to produce the desired (5-oxo-1,3-oxathiolan-2-yl) methyl butanoate., or with 1,4-dithiane-2,5-diol in THF to obtain the 5-acetyloxy derivative.

Method D in FIG. 2 is similar to the method described above illustrated in FIG. 1.

These steps are more fully understood by reference to the following examples, which are not intended to limit the scope of the invention.

EXAMPLE 1

To a 200 gallon reactor equipped with an efficient cooling system was charged methyl tert-butyl ether (MtBE, 278 L), DMAP (391 g, 3.2 moles), triethylamine (102.3 L, 74.4 kg, 736.2 moles) and 2-butene-1,4-diol (26.4 L, 28.2 kg, 320 moles). The stirrer was started and the temperature of the reaction mixture was cooled to approximately 4° C. Butyryl chloride (69.6 L, 71.5 kg, 672 moles) was added to the reaction mixture at such a rate as to maintain the batch temperature below 20° C. The triethylamine hydrochloride precipitates during the addition and the reaction mixture becomes a thick, but movable slurry. Thin layer chromatographic analysis of the reaction mixture (silica gel plate; Analtech No. 02521, eluted with 9:1 hexane/EtOAc, and visualized with PMA stain) indicated the reaction was complete after stirring for an additional hour after the addition was complete. Water (120 L) was added to the reactor, and the resulting mixture was stirred until all of the solids dissolved. The phases were separated. The lower (aqueous) layer was checked by TLC analysis for the absence of product (if product is present, save the layer for future product recovery). The upper, organic layer was washed with water (72 L), saturated aqueous potassium bicarbonate (72 L, checked to make sure the exiting aqueous layer was basic, evaporated, under reduced pressure, to afford 69.4 kg of 2-butene-1,4-dibutyrate (95% yield) as a pale golden oil. The NMR spectrum was consistent with a reference spectrum.

EXAMPLE 2

Ozonolysis of 2-oxoethyl butyrate methyl hemiacetal

To a 12 L, three necked round bottomed flask equipped with a mechanical stirrer, immersion thermometer, oil filled gas outlet bubbler and an ozone inlet tube was charged 2-butene-1,4-dibutyrate (1005.0 g, 4.4 moles) and methanol (5 L). The Ozonia CFS-2 ozone generator, 1200 watts, 1 atmosphere oxygen, flow 1 $m^3/h$, stirrer was started and the mixture was cooled in an ice/methanol bath to −20° C. Ozone bubbled into the solution. The temperature of the mixture rose to −10° C. during the addition of ozone. After two hours, thin layer chromatographic analysis of the reaction mixture (silica gel plate, Analtech No. 02521, eluted with 9:1 hexane/EtOAc and visualized with PMA stain) showed the complete disappearance of the starting material. The stirred reaction mixture was purged with nitrogen for 15 minutes and cooled back down to −20° C. Thiourea (170 g, 2.23 moles, Johnson Matthey I0B16) was added in 17 gram portions over 1.5 hours. The temperature of the mixture rose to 0° C. One hour after the complete addition of thiourea, thin layer chromatography and 1H NMR analysis showed the complete disappearance of the ozonide. The mixture was cooled back down to −20° C. and filtered. The filtrate was evaporated to afford 1.5 kg of 2-oxoethyl butyrate methyl hemiacetal (97% yield) as a pale yellow oil. The NMR spectrum was consistent with a reference spectrum.

EXAMPLE 3

Preparation of 2-Butyryloxymethyl-1,3-oxathiolan-5-one

To a 72-L round-bottom flask equipped with a mechanical stirrer, immersion thermometer, nitrogen inlet, pressure equalizing addition funnel and distillation head was charged toluene (31 L, Fisher) and 2-oxoethyl butyrate methyl hemiacetal (10 kg, 9.3 kg actual correcting for residual MeOH). This starting material is actually a mixture of the acetal, hemiacetal, dimer, and trimer. The stirrer was started and mercaptoacetic acid (4.5 L, 64.7 moles) was added dropwise through the addition funnel over two hours. The temperature of the reaction mixture increased to 28° C. during the addition. Thin layer chromatographic analysis of the reaction mixture (silica gel plate; Analtech No. 02521, eluted with 7:3 hexane/EtOAc, and visualized with PMA stain) indicated the starting material was consumed when the addition was concluded. The mixture was heated to 85° C. (internal temperature). The distillate (5 L of a mixture of toluene and aqueous methanol) was, collected over at 75° C. (head temperature). Thin layer chromatographic analysis of the reaction mixture (silica gel plate; Analtech No. 02521, eluted with 7:3 hexane/EtOAc, and visualized with PMA stain) indicated the reaction was complete after eight hours of heating. The reaction mixture was allowed to cool to room temperature and pumped slowly into a 100-L reactor containing 16 L of stirred saturated aqueous potassium bicarbonate solution. The mixture was stirred for 20 minutes then stopped and the layers were allowed to separate. The organic layer was washed with 6 L of saturated aqueous sodium chloride solution and was evaporated to dryness. The crude product was passed through a 2 inch Pope Scientific wiped-film still (column temperature at 90° C., 0.5 mm vacuum, at a rate of ca. 0.5 kg per hour). Low boiling impurities were in the distillate flask while the product was collected in the bottom flask. The yield was 5.8 kg (53.8%). This material was 92% pure by GC analysis (HP-1 Methyl Silicone Gum Column, nitrogen carrier gas at 50 mL/min, Flame Ionization Detector. 280° C., 65° C. held for 1 min then ramp at 12.5° C./min up to 250° C. and held for 1 min, injection volume: 1–2 µL of an EtOAc solution). The NMR spectrum was consistent with a reference spectrum.

EXAMPLE 4

Preparation of 5-Acetoxy-2-butyryloxymethyl-1-3-oxathiolane

To a 50-L four-neck round-bottom flask equipped with an overhead mechanical stirrer, two $N_2$-bubblers, a stopper and a thermocouple/thermowell was charged with anhydrous THF (4.1 L, Aldrich). To this was added slowly, in 100-g portions, lithium aluminum hydride pellets (334 g; 8.8 mol; Aldrich lot #04414KR). This slurry was further diluted with an additional amount of THF (4.1 L) and allowed to stir for 15 hours. Temperature after addition initially rose to 37° C. and eventually cooled to 22° C. The resulting grey mixture was cooled to −5° C. using an ice/MeOH bath. The stopper was replaced with a 5-L pressure equalizing addition funnel and was charged with a mixture of tert-butanol (2.0 kg; 2.6 L; 27.6 mol) and THF (600 mL). This mixture was slowly added to the reaction mixture over 2.5 hours. Reaction temperature increased to 15.9° C. during the addition. The cooling bath was removed and replaced with a warm water bath, warming the reaction temperature to 33° C. This temperature was maintained for 1.5 hours or until the gas evolution ceased. The reaction mixture was cooled to −6° C. using an ice/MeOH bath. To the addition funnel was charged a mixture of 2-butyloxymethyl-1,3-oxathiolan-5-one [1410.6 g; 6.9 mol and THF (350 mL)]. This mixture was slowly added to the reaction mixture, keeping the internal temperature below 5° C. The reaction was allowed to stir for 1.5 hours at which point an aliquot (five drops of reaction mixture) was quenched with acetic anhydride/4-dimethylaminopyridine and diluted with ethyl acetate (ca. 1 mL). GC analysis of the aliquot mixture (HP-1 Methyl Silicone Gum Column, nitrogen carrier gas at 50 mL/min, Flame Ionization Detector: 280° C., 65° C., held for 1 min then ramp at 12.5° C./min to 250° C. and held for 1 mm injection volume: 1 µL of the quenched reaction mixture) showed no more starting lactone (RT=7.4 minutes). The cooling bath was replenished with fresh ice/MeOH mixture and the reaction was cooled to −9.0° C. To the resulting greenish reaction mixture was added 4-dimethylaminopyridine (42 g; 0.35 mol) in one portion. To the addition funnel was charged acetic anhydride (7065.5 g; 6.5 L; 69.0 mol) in portions. This was slowly added to the reaction mixture over 1.5 hours maintaining the temperature below 0° C. The resulting greenish reaction mixture was allowed to stir for 13 hours while gradually warming it up to 19° C. GC analysis (HP-1 Methyl Silicone Gum Column, nitrogen carrier gas at 50 mL/mm, Flame Ionization Detector. 280° C., 65° C. held for 1 mm then ramp at 12.5° C./min to 250° C. and held for 1 min. injection volume: 1–2 µL of the reaction mixture) showed the reaction to be complete (formation of two new peaks at RT=8.4 and 8.6 minutes).

The brownish-orange reaction mixture was diluted with ethyl acetate (13 L). Half of the reaction mixture was filtered through a pad of celite (7.5 cm thick in an 18-inch table-top funnel). Filtration proceeded extremely slowly. Celite (1.5 kg) was added to the second half of the reaction mixture. This was allowed to stir for four hours and was filtered through a pad of celite using the same protocol as above. The filtration proceeded smoothly. The combined filtrates were transferred to a 72-L drop-bottom flask equipped with an overhead mechanical stirrer. To this was added saturated aqueous sodium bicarbonate solution (20 L). The resulting biphasic mixture was stirred for one hour at which point the layers were separated and the organic layer was washed with an additional saturated aqueous sodium bicarbonate solution (10 L), followed by saturated aqueous sodium chloride solution (20 L). The layers were separated and the organic layer was dried over anhydrous magnesium sulfate (3.0 kg) using a lightning stirrer to agitate the suspension. The magnesium sulfate was removed by vacuum filtration and the filtrate was evaporated in vacuo (35° C. water bath) to afford a red liquid. This was further concentrated using a high vacuum pump (23 mmHg; 40° C.) for 1.5 hours which afforded the crude 5-acetoxy-butyryloxymethyl-1,3-oxathiolane as a red oil (1483.0 g; 87% yield).

A 10-g portion of the crude 5-acetoxy-butyryloxymethyl-1,3-oxathiolane was dissolved in hexane (100 mL, 10 volumes) and stirred vigorously until a small portion of red oil remained on the bottom of the flask. To this stirred mixture was added silica gel (2 g) and this mixture was stirred for 10 minutes. The resulting slurry was filtered through a pad of celite affording a pale yellow filtrate. Evaporation of solvent in vacuo provided 5-acetoxy-butyryloxymethyl-1,3-oxathiolane as a yellow oil (7.7 g; 77% recovery). While the TLC baseline impurities were removed, the GC analysis did not change.

EXAMPLE 5

Condensation of 5-acetoxy-butyryloxymethyl-1,3-oxathiolane with 5-fluorocytosine using iodotrimethylsilane as the Lewis acid A 3-L three necked round bottom flask equipped with a mechanical stirrer, stopper and a water-cooled reflux condenser fitted with a nitrogen bubbler was charged with 5-fluorocytosine (51.6 g, 0.40 mol), hexamethyldisilazane (665 mL, 3.10 mol) and ammonium sulfate (2.0 g). The resultant slurry was heated to reflux for 2.5 h whereupon the formation of a white solid on the inner wall of the condenser was observed. The resulting yellow solution was allowed to cool to room temperature at which time a white solid formed in the reaction solution. The excess hexamethyldisilazane was removed under reduced pressure while maintaining an inert atmosphere. To this white solid was added methylene chloride (890 mL) producing a clear, yellow solution. The reaction vessel was equipped with a thermocouple/thermowell, a claisen head fitted with a pressure equalizing addition funnel and a nitrogen bubbler. The reaction solution was cooled to −5° C. in an ice-methanol bath at which point a solution of oxathiolane acetate (175.6 g (62% pure by GC), 0.41 moL) in methylene chloride (300 mL) was transferred in portions to the addition funnel and subsequently added to the reaction mixture in a dropwise fashion over 45 minutes. The temperature of the reaction solution was maintained between −5° C. and 0° C. Following addition, the addition funnel was rinsed with 100 mL of methylene chloride and this was added to the reaction mixture. A solution of iodotrimethylsilane (89.0 mL, 0.62 mol) in methylene chloride (150 mL) was transferred to the addition funnel and was subsequently added to the reaction mixture over 45 minutes, keeping the internal temperature of the mixture between −5° C. and 0° C. Some white smoke formation was noted during the initial addition, but this soon dissipated toward the end of the addition. The resulting reaction mixture was allowed to warm to room temperature where it was stirred overnight. The reaction mixture was carefully quenched with saturated, aqueous sodium bicarbonate and the resulting layers split. The organic layer was washed with brine and concentrated under reduced pressure affording 228 g of a yellow-brown semi-solid. HPLC analysis showed an approximate 1:1 mixture of α and β anomers. A portion of this material was recrystallized from toluene affording a clean separation of the α and β anomers.

EXAMPLE 6

Removal of Butyrate Protecting Group

An 8.0 g (25 mmol) sample of the butyrate ester (SA.494.89.1) was dissolved in 160 mL of methanol, vigorous stirring was initiated and the solution was immersed in an ice/water bath. After 10 min this solution was treated with 6.4 g of DOWEX SBR strongly basic anion (OH$^-$) exchange resin (Sigma cat# I-9880, p. 1803). After stirring for 3 h the bath was removed and stirring was continued until TLC analysis revealed complete consumption of starting material. The mixture was diluted with 100 mL of methanol and filtered. The resin was washed with 100 mL of methanol and the combined solution was concentrated affording a pale-yellow solid. This solid was triturated with 20 mL of COLD ethyl acetate and the resultant solid was dried affording 5.0 g (81%) of 9/152-15 as an off-white solid.

It should be noted that the resin should be exhaustively washed with methanol, and then dried prior to use. A good TLC system for this reaction is 15% methanol/85% chloroform.

Alternatively, the butyrate ester may be removed by treating the ester with primary or secondary amine in an alcohol solvent. The preferred amines are ammonia and butylamine and the preferred solvent is methanol.

EXAMPLE 7

Synthesis of (5-oxo-1,3-oxathiolan-2-yl) methyl butanoate (25) and (5-acetyloxy-1,3-oxathiolan-2-yl) methyl butanoate (26) from (2,2-dimethyl-1,3-dioxolan-4-yl) methanol Synthesis of (2,2-dimethyl-1,3-dioxolan-4-yl) methyl butanoate (22)

To a well-stirred solution of solketal (21, 62.6 ml, 500 mmol), Et$_3$N (83.6 ml, 600 mmol) and DMAP (5 g, 40.9 mmol) in tert-butyl methyl ether (11) at 0° C., n-butyryl chloride (52.4 mL, 500 mmol) was added dropwise over a 75 minute period. The mixture was stirred for an additional hour at 0° C. and then at room temperature for an additional 5 hours. The mixture was diluted with AcOEt (11), washed with water (11), dried (MgSO$_4$), filtered and evaporated to afford 22 (104.6 g, 500 mmol, 100%) as an oil. The material was used in the next step without any further purification.

Synthesis of 2,3-dihydroxypropyl butanoate (23)

A solution of 22 (50.6 g, 250 mmol), and Dowex 50W X8-100⁻H⁺ resin (76.5 g) in MeOH (500 ml), was heated at 50° C. for 2 hours, cooled to room temperature, filtered, and the resin washed with MeOH (1×200 ml). The methanol fractions were combined and concentrated in vacuo. The crude product was passed through a plug of silica gel using ethyl acetate:hexanes (1:1) as the eluent. Fractions containing the product were combined and concentrated in vacuo to afford 23 (32.8 g, 200 mmol, 81%) as an oil. The material was used in the next step without any further purification.

Synthesis of 2-oxoethyl butanoate (24)

A solution of sodium periodate (89.4 g, 418 mmol) in distilled water (450 ml) was prepared by heating the mixture at 45° C. for approximately 20 minutes. This solution was added dropwise over a 60 minute period to a solution of the diol 23 (30.8 g, 190 mmol) in acetone (225 ml). Once the addition is complete, the mixture is stirred an additional 2 hours at room temperature. The acetone is removed using a rotary evaporator (the bath temperature should not exceed 35° C.). The reaction mixture is diluted with water (250 ml) and the aqueous layer is extracted with AcOEt (3×250 ml). The organic fractions are combined, washed with water (250 ml), dried (MgSO$_4$), filtered, and evaporated (the bath temperature was not allowed to exceed 35° C.) to afford 24 (20.5 g, 157 mmol, 83%) as an oil. The product was used in the next step without any further purification.

Synthesis of (5-oxo-1,3-oxathiolan-2-yl) methyl butanoate (25)

A solution of 24 (3.90 g, 0.030 mol), mercaptoacetic acid (3.32 g, 0.036 mol) and p-TsOH.H$_2$O (0.28 g, 1.5 mmol) in acetonitrile (600 ml) was heated at reflux for 3.5 hours. During the period of reflux, four portions of 25 ml each were drained from a Dean-Stark trap (to remove the water-acetonitrile azeotrope). Analysis of the reaction solution by TLC (6:1 hexane:AcOEt) revealed one major new component and no unreacted aldehyde (visualized by PMA and 2,4-DNP stains). The reaction solution was allowed to stir at room temperature for 16 hours, and then evaporated to dryness. The residue was partitioned between concentrated NaBCO$_3$ (50 ml) and AcOEt (75 ml); the aqueous portion was extracted with additional AcOEt (2×75 ml). The organic fractions were combined, dried (MgSO$_4$), filtered, and concentrated in vacuo. The crude material (6 g) was purified by flash chromatography (125 grams silica gel with 20% ethyl acetate in hexane). Compound 25 (3.27 g, 16 mmol, 53%) was obtained as an oil:TLC (3:1 hexane:AcOEt)—one spot with R$_f$=0.41; $^1$H-nmr (CDCl$_3$)—compatible with structure; mass spectrum (FAB)—m/z=205.1 (M+1).

Synthesis of (5-acetyloxy-1,3-oxathiolan-2-yl) methyl butanoate (26)

To a solution of 25 (0.50 g, 2.5 mmol) in anhydrous THF (15 ml) at −5 to −10° C., a solution of 1.0M lithium tri-t-butoxy aluminum hydride in THF (2.7 ml) was added by syringe pump over 2 hours, while the temperature was maintained at −5 to −10° C. Upon completion of addition, the solution was allowed to stand at 3° C. for 18 hours, and was then warmed to room temperature. DMAP (1.7 mmole, 0.20 g) and acetic anhydride (25.0 mmole, 2.4 ml) were added and the resulting orange solution was stirred at ambient temperature for 3 hours, at which point concentrated NaHCO$_3$ (25 ml) was added. After stirring for 1 hour, the phases were separated, and the aqueous phase was extracted with two additional portions of AcOEt. The organic fractions were combined, dried (MgSO$_4$), filtered and evaporated to afford crude product (0.77 g). After flash chromatography (20 g of silica gel with 20% ethyl acetate in hexane), compound 26 (0.50 g, 2.0 mmol, 80%) was isolated as an oil: TLC (25% ethyl acetate:hexane)—one spot with R$_f$=0.51; $^1$H-nmr (CDCl$_3$)—compatible with structure.

EXAMPLE 8

Synthesis of (5-oxo-1,3-oxathiolan-2-yl) methyl butanoate (25) from (2,2-diethoxy ethanol) (27)
Synthesis of 2,2-diethoxyethyl butanoate (28)

To a well-stirred solution of 27 (Lancaster 6282, 13.4 g, 100 mmol), DMAP (61 mg, 0.5 mmol) and Et$_3$N (16 ml, 11.64 g, 115 mmol) in EtOAc (50 ml) at 0° C. was slowly added n-butyryl chloride (10.90 ml, 11.19 g, 105 mmol). After stirring for 1 hour at room temperature the reaction mixture was diluted with more EtOAc (50 ml), and successively washed with: concentrated NaHCO$_3$ (2×100 ml) and brine (2×100 ml), dried, filtered and evaporated to afford 28 (21.5 g, 100 mmol, 100%) as a yellow liquid that was used in the next step without any further purification.

Synthesis of (5-oxo-1,3-oxathiolan-2-yl) methyl butanoate (25)

A well-stirred solution of 28 (6.13 g, 30 mmol), mercaptoacetic acid (4.14 g, 3.13 ml, 45 mmol) and p-TsOH.H$_2$O (60 mg, 0.31 mmol) in dry toluene was refluxed for 2 hours. Solvent was occasionally removed with a Dean-Stark trap, and fresh dry toluene was added. After cooling to room temperature, the reaction mixture was diluted with AcOEt (50 ml) and successively washed with: concentrated NaHCO$_3$ (2×100 ml) and brine (2×100 ml), dried, filtered and evaporated to afford 25 (5.2 g, 25.5 mmol, 85%) as a yellow liquid that was used in the next step without any further purification.

EXAMPLE 9

Synthesis of (5-oxo-1,3-oxathiolan-2-yl) methyl butanoate (25) and (5-acetyloxy-1,3-oxathiolan-2-yl) methyl butanoate (26) from (2,2-diethoxy ethanol) (27) through 2,2-diethoxyethyl butanoate (28) and 2-oxoethyl butanoate (24)

Synthesis of 2-oxoethyl butanoate (24)

A well-stirred solution of 28 (8.16 g, 40 mmol) in DCM (200 ml) at room temperature, was treated with TFA (44.4 g, 30 ml, 390 mmol) and water (7.2 g, 7.2 ml, 400 mmol). After stirring for 2 hours at room temperature the solution was evaporated at 35° C. It was then coevaporated with hexane several times to remove traces of TFA. Compound 24 (5.2 g, 40 mmol, 100%) was obtained as a colorless liquid, and was used in the next step without any further purification.

Synthesis of (5-oxo-1,3-oxathiolan-2-yl) methyl butanoate (25)

To a well-stirred suspension of 24 (1.3 g, 10 mmol) and CSA (116 mg, 0.50 mmol) in dry DCM (10 ml) was slowly added a solution of mercaptoacetic acid (2.76 g, 2.08 ml, 30 mmol) in dry DCM (5 ml). The reaction was left at room temperature for 16 hours with stirring. The reaction mixture was diluted with DCM (20 ml) and successively washed with: concentrated NaHCO3 (3×30 ml) and brine (2×30 ml), dried, filtered and evaporated to afford 25 (0.9 g, 4.4 mmol, 44%) as a colorless syrup.

Synthesis of (5-acetyloxy-1,3-oxathiolan-2-yl) methyl butanoate (26)

To a well-stirred solution of 24 (2.6 g, 20 mmol) and 1,4-dithiane-2,5-diol (1.68 g, 11 mmol) in dry THF (10 ml) was added $BF_3:Et_2O$ (312 mg, 278 μl, 2.2 mmol). The mixture was stirred for 16 hours at room temperature. The solids were removed by filtration and to the remaining solution was added: dry pyridine (2.3 g, 2.4 ml, 29 mmol), DMAP (18 mg, 0.15 mmol) and then $Ac_2O$ (30 g, 2.77 ml, 29 mmol). The solution was stirred 16 hours at room temperature. The reaction was quenched with 8% HCl and extracted with AcOEt. The organic phase was separated and successively washed with: 8% HCl, brine, concentrated $NaHCO_3$ and brine, dried, filtered and evaporated to afford 26 (3.5 g, 14 mmol, 70%, 60% pure) as a yellowish syrup.

EXAMPLE 10

Synthesis of (5-oxo-1,3-oxathiolan-2-yl) methyl butanoate (25) and (5-acetyloxy-1,3-oxathiolan-2-yl) methyl butanoate (26) from 1,2-diethanol (29)

Synthesis of 2-hydroxyethyl butanoate (30)

To a well-stirred solution of 29 (834 g, 750 ml, 13.5 mol) and $Et_3N$ (116 g, 160 ml, 1.15 mol) at 0° C., was slowly added n-butyryl chloride (22 g, 120 ml, 1.15 mol). The reaction was left with stirring at room temperature for 16 hours.

The solution was diluted with brine (1.5 l), and stirred for an additional hour. It was then extracted with heptane (3×700 ml) to remove the diester. The aqueous layer was extracted with EtOAc (3×600 ml). The combined organic phase was washed with water to remove remaining ethylene glycol (29), dried, filtered and evaporated to afford compound 30 (39.7 g, 0.3 mol, 26%).

Synthesis of 2-oxoethyl butanoate (24)

To a mechanically stirred suspension of $P_2O_5$ (42.53 g, 150 mmol) in dry DCM (100 ml) at 0° C., was slowly added 30 (11.0 g, 83 mmol), followed by DMSO (13 g, 11.8 ml, 166 mmol). After stirring at 0° C. for 1 h, the ice bath was removed and the mixture further stirred at rt for 1.5 h. It was then cooled to 0° C., and then $Et_3N$ (42 g, 58 ml, 416 mmol) was slowly added. The reaction was then left with stirring for 6 hours at room temperature. The reaction was quenched by adding 1.0 HCl (60 ml) at 0° C., and left with stirring for 30 minutes at 0° C. The organic layer was then washed with water (2×250 ml), dried, filtered and evaporated to afford 24 (6.60 g, 51 mmol, 61%) as a yellow liquid, that was used in the next step without any further purification.

Synthesis of (5-oxo-1,3-oxathiolan-2-yl) methyl butanoate (25)

To a well-stirred suspension of 24 (1.3 g, 10 mmol) and CSA (116 mg, 0.50 mmol) in dry DCM (10 ml) was slowly added a solution of mercaptoacetic acid (2.76 g, 2.08 ml, 30 mmol) in dry DCM (5 ml). The reaction was left at room

EXAMPLE 12

Synthesis of [5-(4-amino-5-fluoro-2-oxo-1(2H)-pyrimidinyl)-1,3-oxathiolan-2-yl]methyl butanoate (2R/2S, β) [31 (2R/2S, β)]

temperature for 16 hours with stirring. The reaction mixture was diluted with DCM (20 ml) and successively washed with: concentrated NaHCO₃ (3×30 ml) and brine (2×30 ml), dried, filtered and evaporated to afford 25 (1.4 g, 6.8 mmol, 68%) as a yellow syrup.

Synthesis of (5-acetyloxy-1,3-oxathiolan-2-yl) methyl butanoate (26)

To a well-stirred solution of 24 (2.6 g, 20 mmol) and 1,4-dithiane-2,5-diol (1.68 g, 11 mmol) in dry THF (10 ml) was added BF₃:Et₂O (312 mg, 278 μl, 2.2 mmol). The mixture was stirred for 16 hours at room temperature. The solids were removed by filtration and to the remaining solution was added: dry pyridine (2.3 g, 2.4 ml, 29 mmol), DMAP (18 mg, 0.15 mmol) and then Ac₂O (30 g, 2.77 ml, 29 mmol). The solution was stirred overnight at room temperature. The reaction was quenched with 8% HCl and extracted with AcOEt. The organic phase was separated and successively washed with: 8% HCl, brine, concentrated NaHCO₃ and brine, dried, filtered and evaporated to afford 26 (4.75 g, 19 mmol, 95%, 95% pure) as a yellowish syrup.

III. Coupling of 1,3-Oxathiolane with Protected Base

EXAMPLE 11

Coupling of 1,3-Oxathiolane with Protected Base with TiCl₃(OiPr)

The protected acetate (150 mg, 0.604 mmol, 1 eq) was dissolved in 1.5 mL of anhydrous dichloromethane under Argon atmosphere. In a different container under Argon, bis-silylated cytosine (154 mg, 0.604 mmol, 1 eq) dissolved in 1.5 mL of anhydrous dichloromethane was allowed to mix with 1 equivalent of freshly prepared TiCl₃(OiPr) (from 0.75 eq of TiCl₄ as a 1 M solution in dichloromethane and 0.25 eq of neat Ti(OiPr)₄, both available from Aldrich). The solution of complex of the base and TiCl₃(OiPr) was added dropwise to the acetate and the resulting slightly yellow clear solution allowed to stir at room temperature for about 20 min, after which 0.6 mL of TiCl₄ (1 M solution in dichloromethane from Aldrich) was slowly added. The resulting red solution was allowed to stir at room temperature for about 2 hours followed by addition of 1 mL of ammonium hydroxide. After 30 minutes the mixture was filtered through silica gel, using 4:1-hexane ethyl acetate and 9:1-ethyl acetate:ethanol as eluants, to afford a white foam that after nuclear magnetic resonance analysis corresponds mainly to the protected nucleoside analog, 3TC. In an alternative embodiment, other Lewis acids such as trimethylsilyl triflate and iodotrimethylsilane or a mixture of both could be used in the coupling stage.

Chlorination of racemic acetate: HCl gas was bubbled into a solution of 26 (2R/2S) (49.6 g, 0.2 mol) in Cl₃CH (0.5 L) at 0° C., over a period of 75 minutes. The homogenous dark yellow solution was allowed to stir for 30 minutes whereupon toluene (100 ml) was added, and this solution was concentrated to dryness under reduced pressure at 48° C. This toluene chase was repeated twice. The resultant crude oil was diluted with Cl₃CH (100 ml) and this solution was used for coupling (see below).

Silylation of 5-fluorocytosine: A suspension of 5-fluorocytosine (30.96 g, 0.24 mol), ammonium sulfate (1 g) and 1,1,1,3,3,3-hexamethyldisilazane (100 ml, 0.48 mol) in Cl₃CH (0.5 L) was refluxed for 4 hours whereupon a homogenous solution was obtained. This solution was cooled to room temperature.

Coupling of silylated 5-flurocytosine with racemic chloride: To the solution of the silylated 5-fluorocytosine was added a solution of the racemic chloride. The resulting solution was heated at refluxed for 3 hours and cooled to room temperature. The solution was diluted with EtOAc (300 ml) and concentrated NaHCO₃ (300 ml) was added. The mixture was stirred for 1 hour at room temperature and the layers were separated. The aqueous layer was extracted once with DCM (100 ml) and the combined organic layers were dried (Na₂SO₄), filtered and evaporated to dryness under reduced pressure. The crude material was chromatographed on silica gel affording the desired material 31 (2R/2S) (48.8 g, 77%) as a 3.5:1 mixture of β:α anomers (AUC).

Isolation of β anomer: The 3.5:1 anomer mixture (48.8 g) was added to EtOAc (290 ml). The suspension was heated at reflux for 10 minutes whereupon a homogenous solution was obtained. The oil bath was removed and the solution was seeded with the β anomer (10 mg). The mixture was allowed to stand at room temperature for 2 hours. The resultant white crystals were collected by filtration to afford compound 31 (2R/2S) (25.4 g, 52% recrystallization recovery) as a 97:3 mixture of β:α anomers (AUC) by HPLC.

Oxoacetates other than butyrate, such as benzoate, p-methoxybenzoate and p-(t-butyl)-benzoate, were coupled with silylated 5-fluorocytosine by the same procedure as above to give the corresponding products as 2.2:1, 2.2:1 and 2:1 mixtures of β:α anomers (AUC), respectively.

Any appropriate organic solvent, including toluene, chloroform, acetic acid, THF, ethers, benzene, and other common solvents can be used in the chlorination reaction. No obvious effect of solvents on chlorination or stereoselectivity of final products was observed. However, the stereoselectivity of coupling reaction of oxoacetates with silylated 5-fluorocytosine was greatly affected by solvents. The ratio of β:α anomers (AUC) was 3.0–5.0:1 when above coupling reaction was carried out in chloroform, while 2.8:1 in toluene.

EXAMPLE 13

Synthesis of [5-(4-amino-5-fluoro-2-oxo-1(2H)-pyrimidinyl)-1,3-oxathiolan-2-yl]methyl butanoate (2R, β/α) [31 (2R, β/α)]

1—Chlorination of chiral acetate: To a solution containing chiral acetate 26 (2.7 g, 8.0 mmol) [74% AUC by GC] in 1,2-dichloroethane (40 ml) at 0° C. was added a solution of HCl (16 mmol) in 1,2-dichloroethane (26 ml). After stirring for 0.5 hour, more HCl (8 mmol) in 1,2-dichloroethane (13 ml) was added. This solution was stirred for 1 hour, and further treated with HCl (16 mmol) in 1,2-dichloroethane (26 ml) and stirred for 1 hour. Upon consumption of the acetate, the solution was vigorously degassed with nitrogen for 0.25 hour and stored under nitrogen at 0° C. until needed.

2—Silylation of 5-fluorocytosine: A suspension comprised of 5-fluorocytosine (1.55 g, 12.0 mmol), ammonium sulfate (155 mg) and 1,1,1,3,3,3-hexamethyldisilazane (7.6 ml, 36 mmol) in 1,2-dichloroethane (80 ml) was refluxed for 2 hour. (After approximately 1 hour the mixture had become a pale yellow homogenous solution). Upon completion, the solution was cooled to 0° C. and stored under nitrogen until needed 3—Coupling of silylated 5-fluorocytosine with chiral chloride: The chloride solution generated above was carefully added, under nitrogen, to the silylated base. The resulting turbid mixture was warmed to reflux and therein maintained for 2 hours. The homogenous pale yellow solution was cooled to rt and quenched with ½ volume of concentrated NaHCO₃. After the split, the organic layer was dried (Na₂SO₄), filtered, and concentrated under reduced pressure affording 2.5 grams of a viscous brown oil. This oil was purified via chromatography on silica gel with 5% EtOH:DCM affording 31 (2R) (1.9 g, 76%) as a 60:40 mixture of β:α anomers. Attempts to separate the anomers by fractional crystallization were unsuccessful.

EXAMPLE 14

Synthesis of 4-amino-5-fluoro-1-(2-hydroxymethyl-1,3-oxathiolan-5-yl)-2 (1H)-pyrimidinone (2R, β/α) [32 (2R, β/α)]

A solution of 31 (2R, β/α) (29.61 g, 93.3 mmol), and n-butylamine (30 ml, 304 mmol) in MeOH (400 ml) was stirred 16 hours at room temperature. The reaction was concentrated in vacuo. EtOAc (3×400 ml) was added and removed in vacuo. MeOH (250 ml) was next added and removed in vacuo. The crude product was triturated with DCM (250 ml), filtered, and washed with more DCM (2×100 ml). The product, a tan solid, was dried in a vacuum oven at 45° C. for 1 hour to afford 32 (2R) (18 g, 72 mmol, 77%) as a 60:40 mixture of β:α anomers. The material was used in the next step without further purification. Attempts to separate the anomers by fractional crystallization were unsuccessful.

α:β (−)-FTC HCl salt [32 (2R, β/α) HCl salt] formation

A mixture of (−)-FTC [32 (2R, β/α)] (60:40 of a β:α anomer mixture, 3.0 g) was dissolved in methanol (30 ml), cooled to 0° C., and treated with a 4.0 M solution of HCl in 1,4-dioxane (3.3 ml [1.1×]). The solution was stirred for 20 minutes, and subsequently concentrated to dryness affording an off-white solid.

EXAMPLE 15

α:β (−)-FTC HCl salt [32 (2R, α/β) HCl salt] recrystallization

32
(2R, β/α) HCl salt 32
(2R, β) HCl salt

Crude (−)-FTC HCl salt (32 (2R, β/α) HCl salt) [60:40 of a β:α anomer mixture, 3.0 g] was dissolved in hot EtOH (20 ml). The resultant homogenous solution was left overnight at room temperature. The resulting crystals were then collected. A 0.9 gram sample of pure β material was obtained. The mother liquor was concentrated and this mixture was recrystallized from ethanol affording 0.5 g of the pure α isomer. The combined mother liquors were concentrated and this material was recrystallized from ethanol affording 0.5 g of the β isomer. The combined recovery of 1.4 g of β anomer represents a 78% yield (theoretical yield of the desired β isomer was 1.8 g). Chiral HPLC analysis revealed that no racemization had occurred in the salt formation.

EXAMPLE 16

Synthesis of Emtricitabine ((−)-FTC or 32 (2R, β))

32
(2R, β) HCl salt 32
(2R, β)

To recover the free base, the hydrochloride salt (32 (2R, β) HCl salt) is taken up in ten volumes of methanol and is treated with 3.0 equivalents of IRA-92 resin. The mixture is stirred for 16 hours and the resin filtered. The solvent is removed in vacuo to leave the free base (32 (2R, β)) in 90% yield. Either an AcOEt or THF slurry can obtain further purification.

This invention has been described with reference to its preferred embodiments. Variations and modifications of the invention will be obvious to those skilled in the art from the foregoing detailed description of the invention. It is intended that all of these variations and modifications be included within the scope of the this invention.

We claim:

1. A process for producing a 1,3-oxathiolane nucleoside comprising reacting a 5-O-protected-oxymethyl-1,3-oxathiolane with a silylated nucleoside in the presence of $(Cl)_3Ti(isopropoxide)$.

2. The process of claim 1 wherein the nucleoside is a pyrimidine.

3. The process of claim 1 wherein the nucleoside is a purine.

4. The process of claim 1, wherein the reaction produces a mixture of α and β anomers.

5. The process of claim 1, wherein the reaction produces nucleosides with high β-selectivity.

6. The process of claim 1, wherein the nucleoside is bis-silylated cytosine.

7. The process of claim 4, wherein the mixture of α and β anomers are separated by crystallization.

8. The process of claim 4, wherein the mixture of α and β anomers are separated by chromatography.

9. The process of claim 8, wherein the chromatography is achiral.

10. The process of claim 8, wherein the chromatography is chiral.

11. The process of claim 1, wherein the 5-O-protected-oxymethyl-1,3-oxathiolane has a 5-O-acyl moiety selected from the group consisting of acetate, propionate, butyrate, benzoate, p-methoxybenzoate and p-(t-butyl)-benzoate.

12. The process of claim 1, wherein the nucleoside is 6-alkylpurine, $N^6$-alkylpurine, $N^6$-acylpurine, $N^6$-benzylpurine, 6-halopurine, $N^6$-acetylenic purine, $N^6$-acylpurine, $N^6$-hydroxyalkylpurine, 6-thioalkyl purine, $N^2$-alkylpurine, $N^4$-alkyl-pyrimidine, $N^4$-acylpyrimidine, 4-halopyrimidine, $N^4$-acetylenic pyrimidine, 4-aminopyrimidine, $N^4$-acylpyrimidine, 4-hydroxyalkylpyrimidine, 4-thioalkylpyrimidine, thymine, cytosine, 6-azapyrimidine, 6-azacytosine, 2-mercaptopyrmidine, 4-mercaptopyrimidine, uracil, $C^5$-alkylpyrimidine, $C^5$-benzylpyrimidine, $C^5$-halopyrimidine, $C^5$-vinylpyrimidine, $C^5$-acetylenic pyrimidine, $C^5$-acylpyrimidine, $C^5$-hydroxyalkyl purine, $C^5$-amidopyrimidine, $C^5$-cyanopyrimidine, $C^5$-nitropyrimidine, $C^5$-amino-pyrimidine, $N^2$-alkylpurine, $N^2$-alkyl-6-thiopurine, 5-azacytosine, 5-azauracil, triazolopyridinyl, imidazolopyridinyl, pyrrolopyrimidinyl, pyrazolopyrimidinyl, 5-fluorocytosine, adenine, guanine, xanthine, 2,6-diaminopurine, 6-aminopurine, 6-chloropurine or 2,6-dichloro-purine.

13. The process of claim 1, wherein the nucleoside is cytosine, 5-fluorocytosine, uracil, thymine, adenine, guanine, xanthine, 2,6-diaminopurine, 6-aminopurine, 6-chloropurine or 2,6-dichloropurine.

14. The process of claim 1, wherein the nucleoside is 5-fluorocytosine.

* * * * *